US011576629B1

(12) United States Patent
Heukensfeldt Jansen

(10) Patent No.: US 11,576,629 B1
(45) Date of Patent: Feb. 14, 2023

(54) SYSTEM AND METHOD FOR ADAPTIVE COINCIDENCE PROCESSING FOR HIGH COUNT RATES

(71) Applicant: GE PRECISION HEALTHCARE LLC, Wauwatosa, WI (US)

(72) Inventor: Floribertus Philippus Martinus Heukensfeldt Jansen, Ballston Lake, NY (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 26 days.

(21) Appl. No.: 17/400,265

(22) Filed: Aug. 12, 2021

(51) Int. Cl.
*G01T 1/20* (2006.01)
*A61B 6/03* (2006.01)
*G06T 11/00* (2006.01)
*A61B 6/00* (2006.01)

(52) U.S. Cl.
CPC ............ *A61B 6/037* (2013.01); *A61B 6/4275* (2013.01); *G01T 1/2018* (2013.01); *G06T 11/003* (2013.01)

(58) Field of Classification Search
CPC ..... A61B 6/037; A61B 6/4275; G01T 1/2018; G06T 11/003
See application file for complete search history.

(56) References Cited

U.S. PATENT DOCUMENTS

| | | | |
|---|---|---|---|
| 7,321,122 B2 | 1/2008 | Bryman | |
| 9,291,725 B2 | 3/2016 | Wang et al. | |
| 9,332,952 B2 | 5/2016 | Prevrhal et al. | |
| 2013/0299704 A1* | 11/2013 | Nakazawa | ............ G01T 1/2985 250/362 |

FOREIGN PATENT DOCUMENTS

| | | | | |
|---|---|---|---|---|
| CN | 111833409 A | * | 10/2020 | |
| EP | 2392946 B1 | * | 9/2017 | ........... G01T 1/1611 |
| JP | 2010002235 A | | 1/2010 | |
| KR | 20070085387 A | | 8/2007 | |

OTHER PUBLICATIONS

Biograph Vision Quadra website downloaded Aug. 11, 2021 (12 pgs); https://www.siemens-healthineers.com/en-us/molecular-imaging/pet-ct/biograph-vision-quadra.

* cited by examiner

*Primary Examiner* — Kiho Kim
(74) *Attorney, Agent, or Firm* — Fletcher Yoder P.C.

(57) ABSTRACT

A method for adaptive coincidence data processing is provided. The method includes detecting positron annihilation events with a detector array of a positron emission tomography (PET) scanner, wherein the PET scanner includes multiple detector rings disposed along a longitudinal axis of the PET scanner, and each detector ring includes multiple detectors. The method also includes, within a given time period, dynamically adjusting a number of positron annihilation events accepted and transmitted to acquisition circuitry for processing utilizing a numerical difference in detector rings along the longitudinal axis between a first detector and a second detector detecting respective annihilation photons from a positron annihilation event.

20 Claims, 5 Drawing Sheets

SYSTEM AND METHOD FOR ADAPTIVE COINCIDENCE PROCESSING FOR HIGH COUNT RATES

BACKGROUND

The subject matter disclosed herein relates to imaging systems, and more particularly to positron emission tomography (PET) imaging systems.

A PET system generates images that represent the distribution of positron-emitting nuclides within the body of a patient. When a positron interacts with an electron by annihilation, the entire mass of the positron-electron pair is converted into two 511 keV photons. The photons are emitted in opposite directions along a line of response. The annihilation photons are detected by detectors that are placed along the line of response on a detector ring. When these photons arrive and are detected at the detector elements at the same time, this is referred to as coincidence. An image is then generated, based on the acquired image data that includes the annihilation photon detection information.

A desired for greater sensitivity in PET (in particular, three-dimensional (3-D)) has led to an increase in the axial field of view (FOV) of PET scanners along the longitudinal axis of the scanners. This higher sensitivity leads to much higher rates of coincidence counts at a given activity level. However, data acquisition is limited by the available bandwidth of the implemented hardware and the high count rates increase the demands placed on the data acquisition electronics. Throttling (i.e., randomly dropping events when the number of events exceeds a transmittal rate for events) may occur to manage these demands. However, this may give more weight to less desirable random events.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a method for adaptive coincidence data processing is provided. The method includes detecting positron annihilation events with a detector array of a positron emission tomography (PET) scanner, wherein the PET scanner includes multiple detector rings disposed along a longitudinal axis of the PET scanner, and each detector ring includes multiple detectors. The method also includes, within a given time period, dynamically adjusting a number of positron annihilation events accepted and transmitted to acquisition circuitry for processing utilizing a numerical difference in detector rings along the longitudinal axis between a first detector and a second detector detecting respective annihilation photons from a positron annihilation event.

In another embodiment, a system for adaptive coincidence data processing is provided. The system includes a memory encoding processor-executable routines. The system also includes a processing component configured to access the memory and to execute the processor-executable routines, wherein the routines, when executed by the processing component, cause the processing component to perform actions. The actions include detecting positron annihilation events with a detector array of a positron emission tomography (PET) scanner, wherein the PET scanner includes multiple detector rings disposed along a longitudinal axis of the PET scanner, and each detector ring includes multiple detectors. The actions also include, within a given time period, dynamically adjusting a number of positron annihilation events accepted and transmitted to acquisition circuitry for processing utilizing a numerical difference in detector rings along the longitudinal axis between a first detector and a second detector detecting respective annihilation photons from a positron annihilation event.

In a further embodiment, a non-transitory computer-readable medium, the computer-readable medium including processor-executable code that when executed by a processor, causes the processor to perform actions. The actions include detecting positron annihilation events with a detector array of a positron emission tomography (PET) scanner, wherein the PET scanner includes multiple detector rings disposed along a longitudinal axis of the PET scanner, and each detector ring includes multiple detectors. The actions also include, within a given time period, dynamically adjusting a number of positron annihilation events within a given time period accepted and transmitted to acquisition circuitry for processing utilizing a numerical difference in detector rings along the longitudinal axis between a first detector and a second detector detecting respective annihilation photons from a positron annihilation event by comparing the numerical difference in detector rings for a given positron annihilation event to an acceptable numerical difference in detector rings along the longitudinal axis, wherein the acceptable numerical difference in detector rings corresponds to an axial angle of acceptance for detected positron annihilation events.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Various embodiments provide systems and methods for adaptive coincidence data processing. In particular, the disclosed embodiments enable dynamic adjustment of the acceptance criteria of events during a scan to enable the preservation of the most valuable events (e.g., events that come out perpendicular to the body or subject being imaged and, thus, experience less attenuation). In particular, the Z span or Z difference between detectors along a longitudinal axis of the PET scanner that detect the corresponding annihilation photons or photons of a positron annihilation event may be dynamically adjusted to regulate accepted events at high count rates. This enables preservation of the most valuable events while reducing throughput requirements. In addition, by communicating the acceptance information in a compact manner with the raw data, reconstruction algorithms can account for the selectively dropped events in a way that enables quantitatively accurate reconstruction. Further, since the scanner will automatically adjust itself to maximize the available bandwidth while preserving the most valuable events, there is no need for separate modes (e.g., high sensitivity mode versus high count rate mode), which is useful for certain scans (e.g., cardiac scans) where the initial count rate is very high but in a later phase maximal sensitivity is needed.

Figure 1:
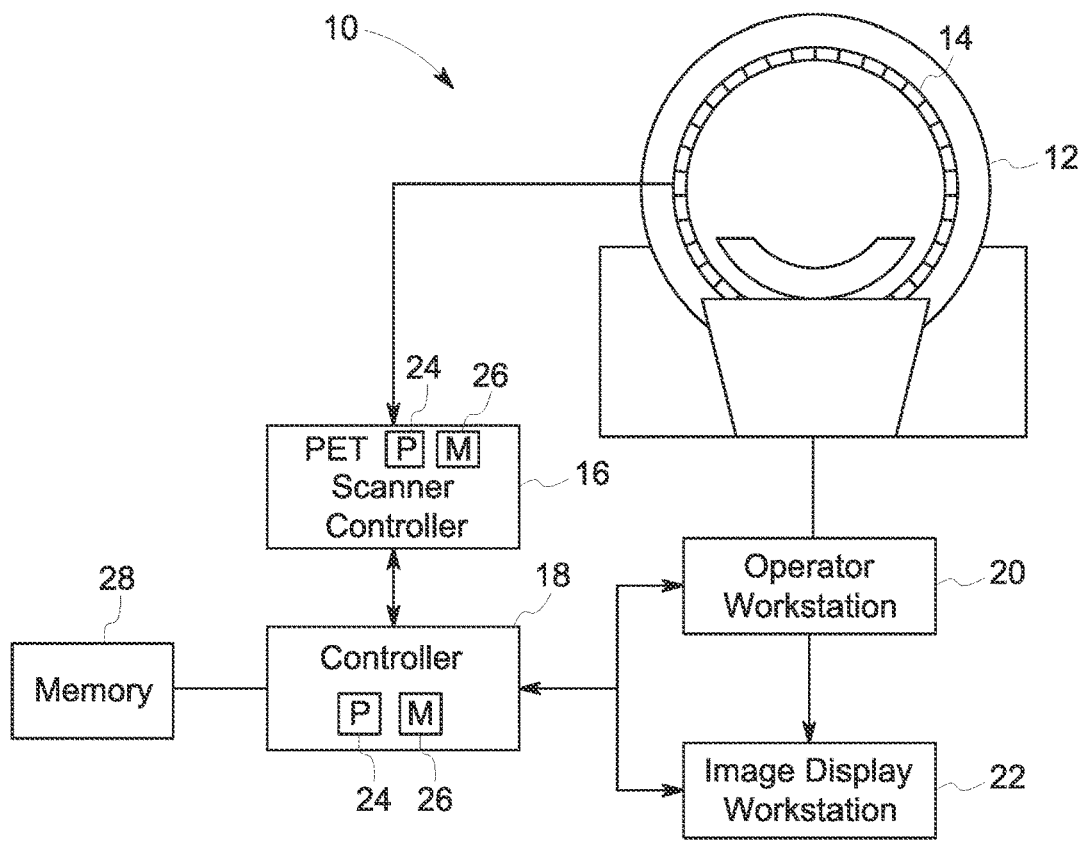
FIG. 1 is a diagrammatical representation of an embodiment of a positron emission tomography (PET) imaging system, in accordance with aspects of the present disclosure.

With the foregoing in mind and turning now to the drawings, FIG. 1 depicts a PET system 10 operating in accordance with certain aspects of the present disclosure. The PET imaging system of FIG. 1 may be utilized with a dual-modality imaging system such as a PET/CT imaging or PET/MRI imaging.

Returning now to FIG. 1, the depicted PET system 10 includes a detector array 12. The detector array 12 of the PET system 10 typically includes a number of detector modules or detector channels (generally designated by reference numeral 14) arranged in one or more rings, as depicted in FIG. 1. Each detector module may include a scintillator block and a photomultiplier tube (PMT) or other light sensor (e.g. silicon photomultiplier). The depicted PET system 10 also includes a PET scanner controller 16, a controller 18, an operator workstation 20, and an image display workstation 22 (e.g., for displaying an image). In certain embodiments, the PET scanner controller 16, controller 18, operator workstation 20, and image display workstation 22 may be combined into a single unit or device or fewer units or devices.

The PET scanner controller 16, which is coupled to the detector array 12, may be coupled to the controller 18 to enable the controller 18 to control operation of the PET scanner controller 16. Alternatively, the PET scanner controller 16 may be coupled to the operator workstation 20 which controls the operation of the PET scanner controller 16. In operation, the controller 18 and/or the workstation 20 controls the real-time operation of the PET system 10. One or more of the PET scanner controller 16, the controller 18, and/or the operation workstation 20 may include a processor 24 and/or memory 26. In certain embodiments, the PET system 10 may include a separate memory 28. The detector 12, PET scanner controller 16, the controller 18, and/or the operation workstation 20 may include detector acquisition circuitry for acquiring image data from the detector array 12 and image reconstruction and processing circuitry for image processing. The circuitry may include specially programmed hardware, memory, and/or processors.

The processor 24 may include multiple microprocessors, one or more "general-purpose" microprocessors, one or more special-purpose microprocessors, and/or one or more application specific integrated circuits (ASICS), system-on-chip (SoC) device, or some other processor configuration. For example, the processor 24 may include one or more reduced instruction set (RISC) processors or complex instruction set (CISC) processors. The processor 24 may execute instructions to carry out the operation of the PET system 10. These instructions may be encoded in programs or code stored in a tangible non-transitory computer-readable medium (e.g., an optical disc, solid state device, chip, firmware, etc.) such as the memory 26, 28. In certain embodiments, the memory 26 may be wholly or partially removable from the controller 16, 18.

By way of example, PET imaging is primarily used to measure metabolic activities that occur in tissues and organs and, in particular, to localize aberrant metabolic activity. In PET imaging, the patient is typically injected with a solution that contains a radioactive tracer. The solution is distributed and absorbed throughout the body in different degrees, depending on the tracer employed and the functioning of the organs and tissues. For instance, tumors typically process more glucose than a healthy tissue of the same type. Therefore, a glucose solution containing a radioactive tracer may be disproportionately metabolized by a tumor, allowing the tumor to be located and visualized by the radioactive emissions. In particular, the radioactive tracer emits positrons that interact with and annihilate complementary electrons to generate pairs of annihilation photons. In each annihilation reaction, two annihilation photons traveling in opposite directions are emitted. In a PET imaging system 10, the pair of annihilation photons are detected by the detector array 12 configured to ascertain that two annihilation photons detected sufficiently close in time are generated by the same annihilation reaction. Due to the nature of the annihilation reaction, the detection of such a pair of annihilation photons may be used to determine the line of response (LOR) along which the annihilation photons traveled before impacting the detector, allowing localization of the annihilation event to that line. By detecting a number of such annihilation photon pairs, and calculating the corresponding lines traveled by these pairs, the concentration of the radioactive tracer in different parts of the body may be estimated and a tumor, thereby, may be detected. Therefore, accurate detection and localization of the annihilation photons forms a fundamental and foremost objective of the PET system 10.

Figure 2:
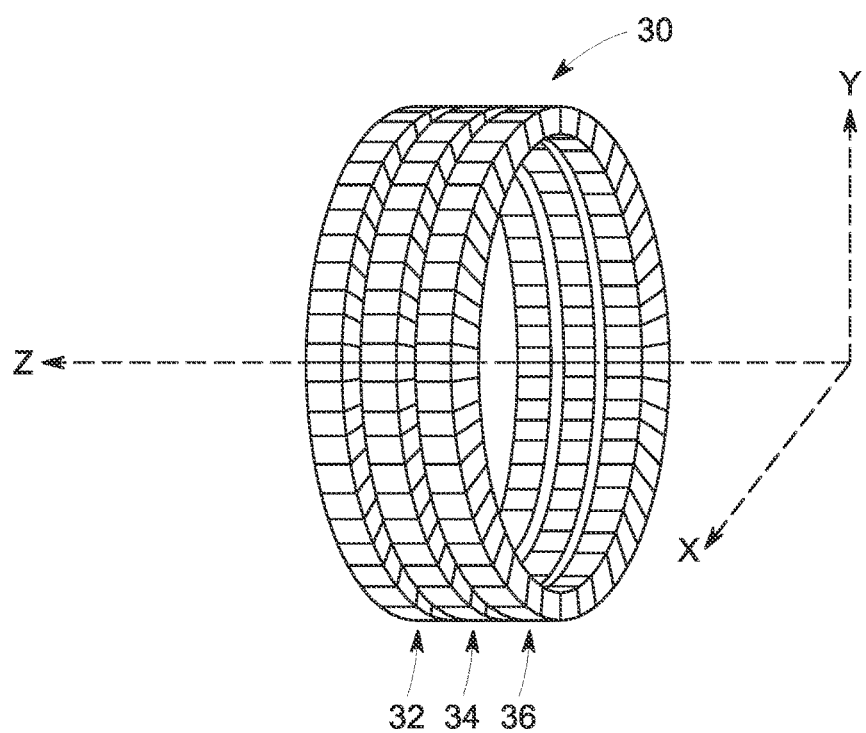
FIG. 2 is a schematic of an embodiment of a 3-D PET scanner, in accordance with aspects of the present disclosure.

Data associated with coincidence events along a number of LORs may be collected and further processed to reconstruct two-dimensional (2-D) tomographic images. Most modern PET scanners can operate in a 3-D mode, where coincidence events from different detector rings positioned along the axial direction are counted to obtain 3-D tomographic images. For example, a PET scanner 30 with multiple detector rings is shown in FIG. 2, where the PMTs are not shown. As shown, the PET scanner 30 comprises three detector rings 32, 34 and 36. The number of detector rings may vary.

Figure 3:
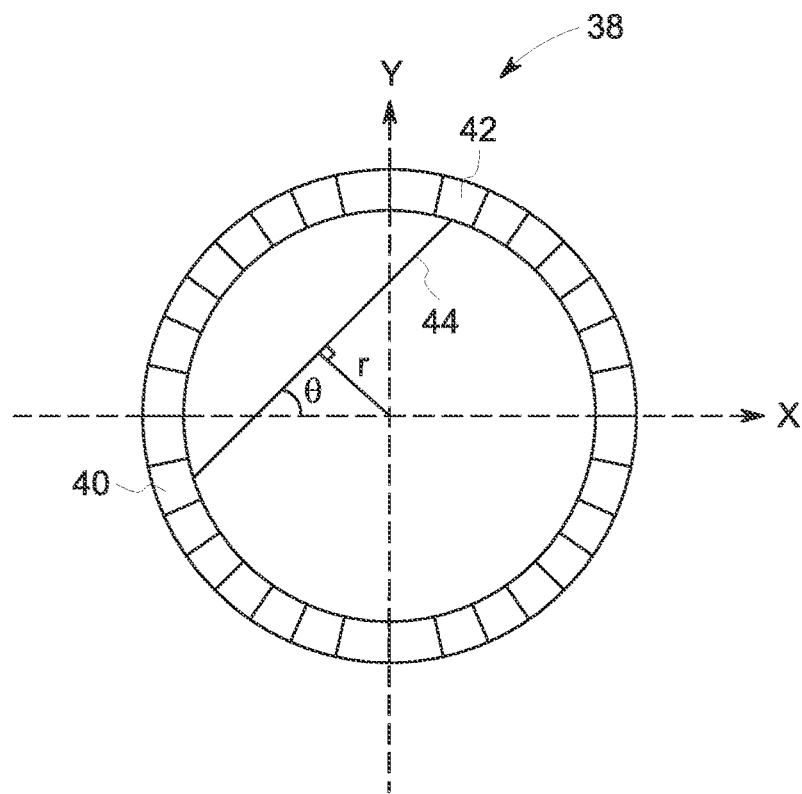
FIG. 3 is a schematic of a line of response (LOR) in a PET imaging system, in accordance with aspects of the present disclosure.

Traditionally, data associated with coincidence events are stored in the form of sinograms based on their corresponding LORs. For example, in a 2-D PET scanner 38 like the one illustrated in FIG. 3, if a pair of coincidence events are detected by two opposite detectors 40 and 42, an LOR may be established as a straight line 44 linking the two detectors 40, 42. This LOR may be identified by two coordinates (r, θ), wherein r is the radial distance of the LOR from the center axis of the detector ring 300, and θ is the trans-axial angle between the LOR and the X-axis. The detected coincidence events may be recorded in a 2-D matrix λ(r, θ). As the PET scanner continues to detect coincidence events along various LORs, these events may be binned and accumulated in their corresponding elements in the matrix λ(r, θ). The result is a 2-D sinogram λ(r, θ), each element of which holds an event count for a specific LOR. In a 3-D PET scanner, an LOR is defined by four coordinates (r, θ, φ, z), wherein the third coordinate φ is the axial angle between the LOR and the center axis (or Z-axis as shown in FIG. 2) of the detector rings and z is the distance of the LOR from the center of the detector along the Z-axis. Typically the third and fourth co-ordinates are combined into only one variable, v, which can define both φ and z coordinates. In this case, the detected coincidence events are stored in a 3-D sinogram λ(r, θ, v).

Large axial FOV scanners have a very high sensitivity which can lead to extreme singles and coincidences count rates. In order to preserve bandwidth, it is desirable to reduce the number of events transmitted to acquisition circuitry for processing. As proposed herein, a throttle (based on a Z span between detector rings detecting a coincidence event) is set on event rates, where N events per millisecond (ms) are transmitted to the acquisition circuitry while the rest of the events are dropped. As described in greater detail below, besides the transmitted events, a counter is sent along to indicate how many events were lost to enable subsequent calculations to correct for dropped events and maintain an accurate calculation.

Figure 4:
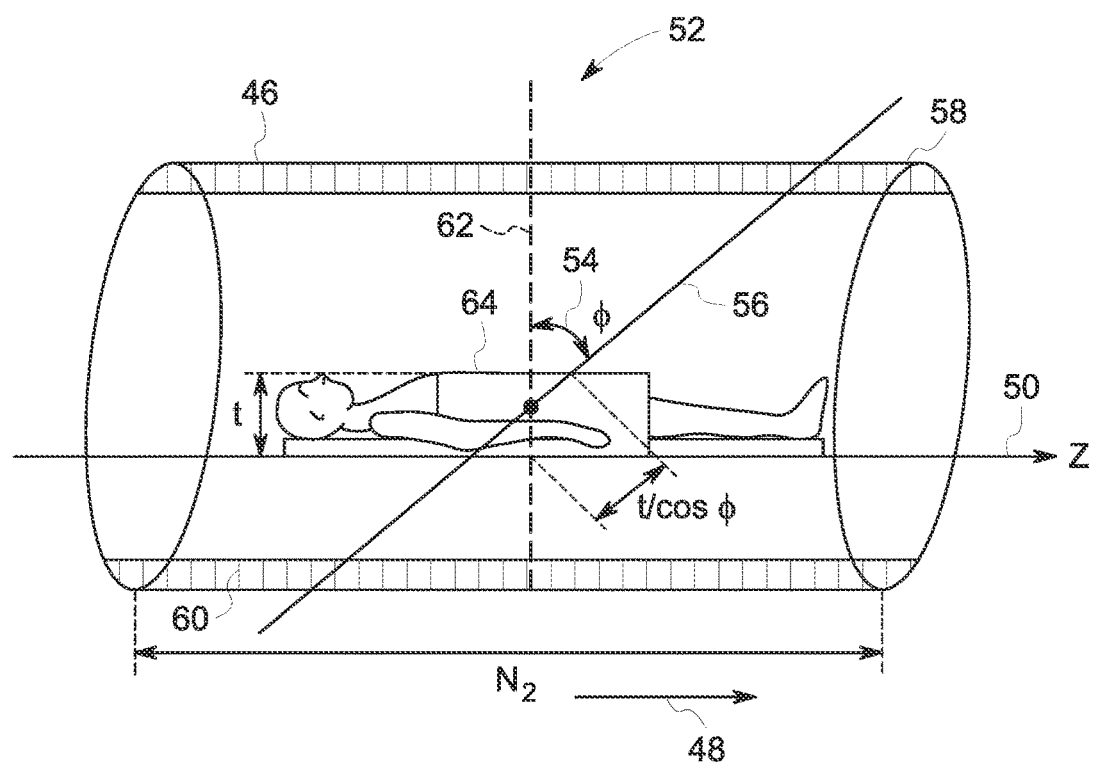
FIG. 4 is a schematic illustration of the effect of a line of response angle on attenuation in a subject.

In addition to throttling events, it is desirable to maintain the most valuable events. For example, as depicted in FIG. 4, assume a number of detector blocks 46 (e.g., scintillator crystals) disposed in an axial direction 48 along a longitudinal axis 50 or Z-axis of a scanner is $N_Z$, where each detector block 46 in the axial direction 48 is part of a respective detector ring. A fully 3-D acquisition enables a ring difference of $\pm(N_Z-1)$. Assuming the scanner 52 includes an axial FOV of 64 centimeters (cm) and a bore of 75 cm, an angle 54 of a central bin of the most extreme oblique plane 56 for a respective LOR between detector modules 58 and 60 relative to an axial plane 62 that is perpendicular to the longitudinal axis 50 and aligned with a central detector ring of the scanner 52 is approximately 40 degrees (a tan (64/75)). For a patient or subject 64 having a thickness, t, of approximately 25 cm, the additional attenuation length for the oblique angle plane is about 8 cm. This additional attenuation length results in a corresponding additional attenuation of about approximately 45 percent. In contrast, a more perpendicular LOR relative to the longitudinal axis 50 (e.g., along plane 62) would be less attenuated and of more value than the LOR 56. Rejecting an event associated with LOR 56 would have relatively less impact on the true rate of detected coincidence events than rejecting an event with a more perpendicular LOR. Indeed, rejecting such an LOR (such as LOR 56) may improve the noise equivalent count rate (NECR) when the randoms rate becomes sufficiently high.

As described herein, an acceptance criteria for events is adjusted on the fly to preserve the most valuable events. In particular, a Z difference or differential, $Z_{diff}$ (e.g., numerical difference) in detector rings along the longitudinal axis 50 between detectors detecting respective annihilation photons from a positron annihilation event may be adjusted. The $Z_{diff}$ is associated with an axial angle of acceptance for detected positron annihilation events. For example, a smaller $Z_{diff}$ is associated with a smaller axial angle of acceptance and a larger $Z_{diff}$ is associated with a larger axial angle of acceptance. This enables the number of positron events within a given time period accepted and transmitted to the acquisition circuitry for processing (e.g., event rate) to be adjusted while giving more weight to events that are more perpendicular to the body and that have experienced less attenuation (as opposed to random events). Dynamically adjusting the $Z_{diff}$ or Z span of accepted events (which acts as a Z throttle) during high count rate periods enables the most valuable evens to be preserved while reducing throughput requirements. It should be noted that the axial angle of acceptance that a particular LOR makes to the Z axis is a function of both the ring difference and the radial distance from the center.

Figure 5:
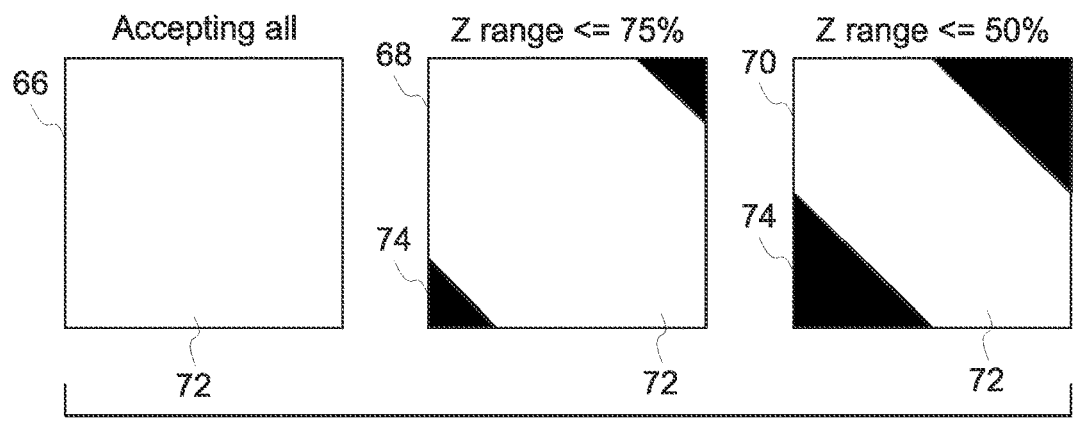
FIG. 5 is a schematic illustration of the effect limiting a Z span has on detection sensitivity, in accordance with aspects of the present disclosure.
Figure 6:
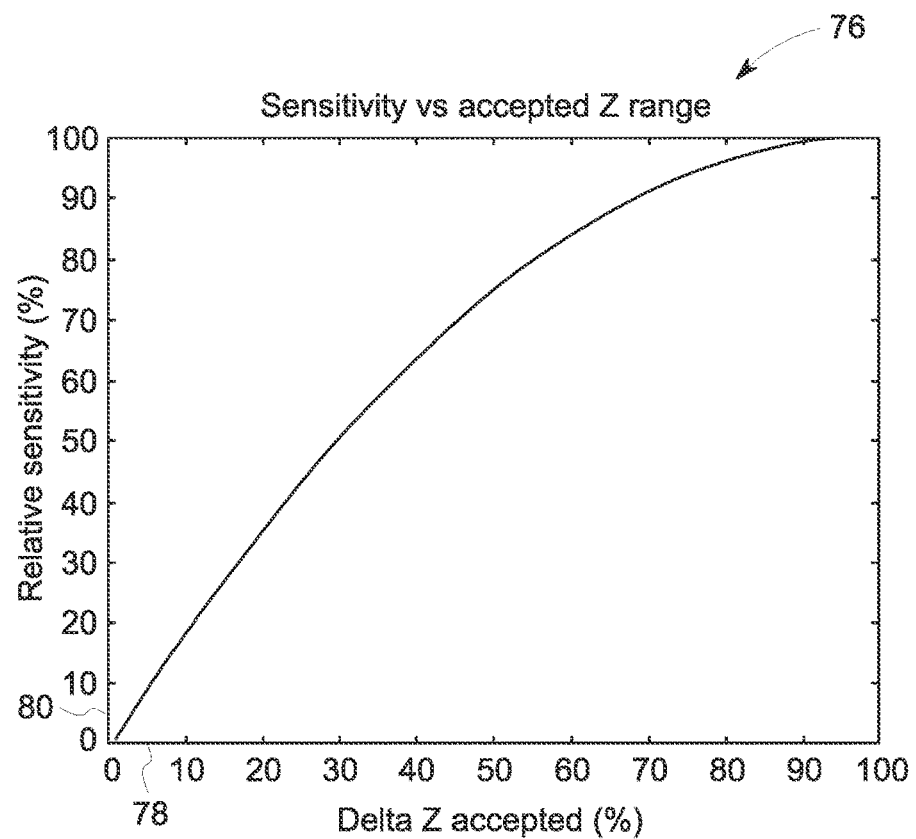
FIG. 6 is a graphical illustration of detection sensitivity versus a Z span of accepted events, in accordance with aspects of the present disclosure.

The effect of the Z throttle on sensitivity/count rate is illustrated in FIGS. 5 and 6. The data in FIGS. 5 and 6 relate to a hypothetical system with 100 Z planes for detecting events within a large axial FOV scanner. FIG. 5 is a schematic illustration of the effect limiting the Z span has on detection sensitivity. FIG. 5 includes $N_Z \times N_Z$ square matrices 66, 68, and 70, respectively. The matrices 66, 68, 70 each include all possible combinations of $(z_1, z_2)$ pairs of detector modules for detecting a respective positron annihilation event. FIG. 5 enables the visualization of the effect of limiting the Z span on sensitivity assuming a pair combination is equally likely. In matrix 66, the entire Z span of the detector region along the axial FOV of an axial scanner is utilized to accept events (i.e., all of the detectors are live) providing maximum sensitivity as indicated by light region 72. In matrix 68, approximately 75 percent of the Z span of the detector region along the axial FOV of the axial scanner is utilized to accept events, where the dark region 74 indicates excluded combinations utilized in accepting events. In matrix 70, approximately 50 percent of the Z span of the detector region along the axial FOV of the axial scanner is utilized to accept events. As depicted in matrix 70, the dark region 74 is larger and the light region 72 is smaller compared to matrix 68 indicating the decrease in sensitivity with the decrease in Z span for accepted events. FIG. 6 is a graphical illustration of detection sensitivity versus a Z span of accepted events. Graph 76 in FIG. 6 includes an X-axis 78 representing the percentage of the Z range of accepted events and a Y-axis 80 representing the relative sensitivity (as a percentage). As indicated by the graph 76, the loss in sensitivity is quadratically related to a reduction in the Z span of accepted events.

Figure 7:
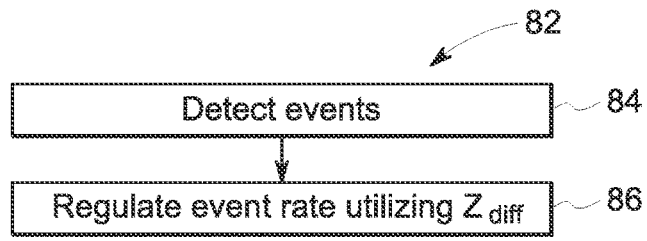
FIG. 7 is a flow chart of an embodiment of a method for adaptive coincidence data processing, in accordance with aspects of the present disclosure.

As mentioned above, dynamically adjusting the $Z_{diff}$ or Z span of accepted events (which acts as a Z throttle) during high count rate periods enables the most valuable events to be preserved while reducing throughput requirements. In particular, this enables adaptive coincidence data processing. FIG. 7 is a flow chart of an embodiment of a method 82 for adaptive coincidence data processing. The method 82 may be performed by one or more components of the PET system 10 in FIG. 1. The method 82 includes detecting positron annihilation events with a detector array of a PET scanner (block 84). The PET scanner includes a plurality of detector rings disposed along a longitudinal axis of the PET scanner, and each detector ring includes a plurality of detectors (e.g., see FIG. 2). The method 82 also includes, within a given time period, dynamically adjusting or regulating a number of positron annihilation events accepted and transmitted to acquisition circuitry for processing (i.e., event rate) utilizing a numerical difference in detector rings (e.g., $Z_{diff}$) along the longitudinal axis between a first detector and a second detector detecting respective annihilation photons from a positron annihilation event (block 86).

In certain embodiments, dynamically adjusting the number of positron annihilation accepted and transmitted includes comparing the numerical difference in detector rings for a given positron annihilation event to an acceptable numerical difference in detector rings along the longitudinal axis. As noted above, the acceptable numerical difference in detector rings corresponds to an axial angle of acceptance for detected positron annihilation events. The given positron annihilation event is accepted and transmitted when the numerical difference in detector rings for the given positron annihilation event falls within the acceptable numerical difference in detector rings. The given positron annihilation event is dropped when the numerical difference in detector rings for the given positron falls outside the acceptable numerical difference in detector rings.

In certain embodiments, dynamically adjusting the number of positron annihilation events accepted and transmitted includes comparing the number of positron annihilation events within the given time period accepted and transmitted to a threshold (e.g., representing a desired maximum number of accepted events or event cutoff number) and adjusting the acceptable numerical difference in detector rings based on the comparison. For example, the numerical difference in detector rings may be decreased when the number of positron annihilation events within the given time period accepted and transmitted is greater than the threshold. The numerical difference in detector rings may be increased when the number of positron annihilation events within the given time period accepted and transmitted is less than the threshold.

Figure 8:
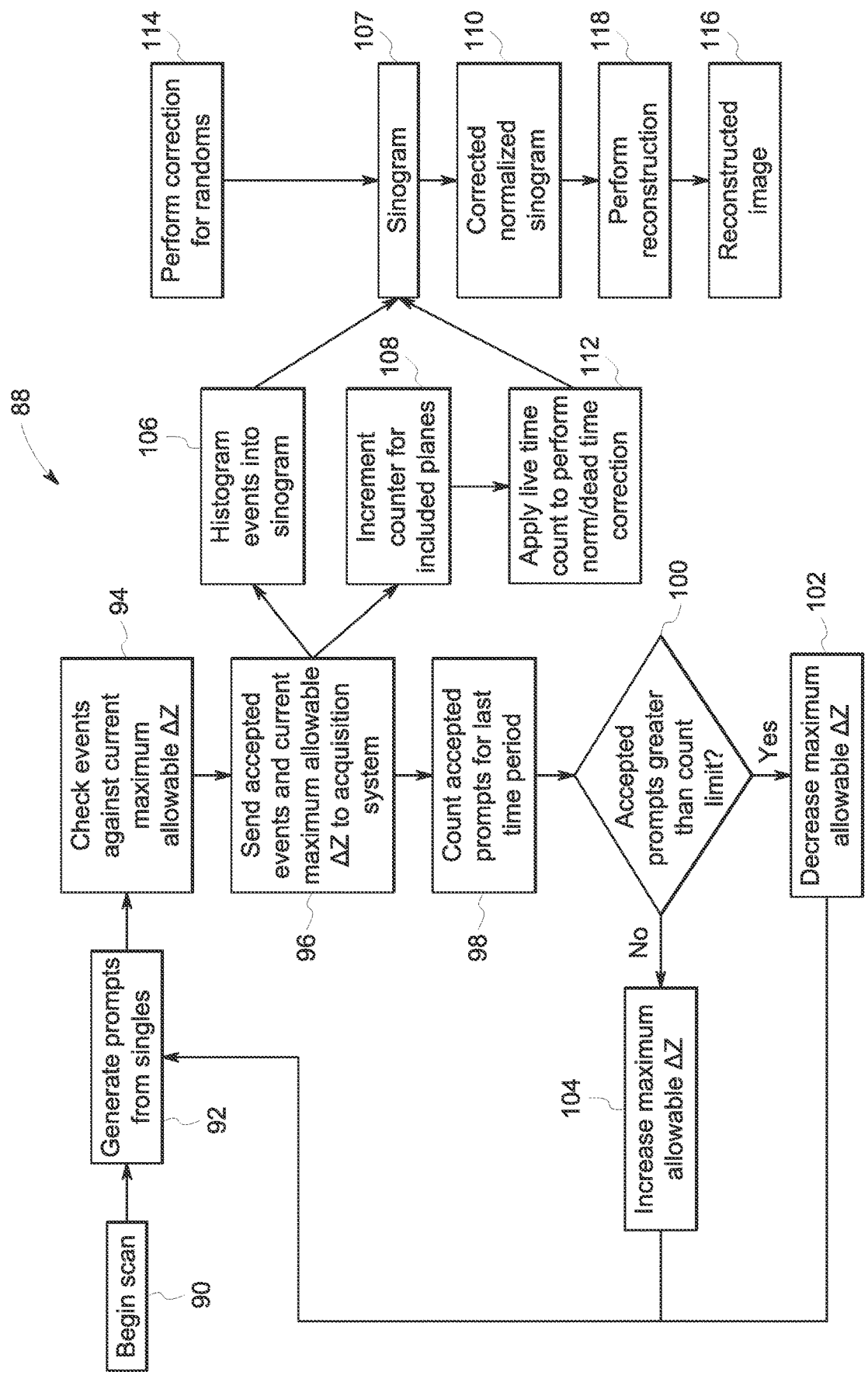
FIG. 8 is a flow chart of an embodiment of a method for adaptive coincidence data processing, in accordance with aspects of the present disclosure.

FIG. 8 is a flow chart of an embodiment of another method 88 for adaptive coincidence data processing. The method 88 may be performed by one or more components of the PET or SPECT system 10 in FIG. 1. The method 88 includes beginning a scan (block 90) of a subject to detect positron annihilation events utilizing a PET scanner that includes a plurality of detector rings disposed along a longitudinal axis of the PET scanner, and each detector ring includes a plurality of detectors (e.g., see FIG. 2). The method 88 includes generating prompts from detected singles (block 92). Each prompt is equivalent to a detected event. The method 88 also includes checking respective events against a current maximum allowable $Z_{diff}$ or $\Delta Z$ (block 94). If an event occurs outside the $Z_{diff}$ (and its corresponding angle of acceptance), the event is dropped. If an event occurs within the $Z_{diff}$ (and its corresponding angle of acceptance), the event is accepted. The method 88 further includes sending accepted events (including list data such as timing and positional data related to detection) and/or associated current maximum allowable $Z_{diff}$ to the acquisition system for processing (block 96). In certain embodiments, the processing circuitry at the acquisition system, may be able to determine the maximum allowable Zdiff associated with certain events (as the accepted events will all be within a certain Z-limit or acceptance angle for a certain time period or timing window). Blocks 92-96 may occur for a given time period (e.g., 1/10 of a second).

The method 88 includes counting the accepted prompts (or events) for the last time period (block 98). The number of accepted prompts may then be compared to a threshold (e.g., count limit) (block 100). If the number of accepted prompts is greater than the count limit, the maximum allowable $Z_{diff}$ may be decreased by an appropriate amount (e.g., 1) to get the number of accepted events in the next time period to be near the threshold (block 102). Following the decrease in $Z_{diff}$, the method 88 returns to block 92. In certain embodiments, the appropriate amount may be different (e.g., 2, 3, etc.). If the number of accepted prompts is less than the count limit, the maximum allowable $Z_{diff}$ may be increased by an appropriate amount (e.g., 1) to get the number of accepted events in the next time period to be near the threshold (block 104). Following the increase in $Z_{diff}$, the method 88 returns to block 92. In certain embodiments, the appropriate amount may be different (e.g., 2, 3, etc.). In certain embodiments, if the number of accepted events is at or near the count limit, the $Z_{diff}$ may not be altered.

As mentioned above, the method 88 includes sending accepted events (including list data such as timing and positional data related to detection) and associated current maximum allowable $Z_{diff}$ to the acquisition system where the unlisting and reconstruction process may occur. The accepted events and associated information (e.g., list data, current maximum allowable $Z_{diff}$, etc.) are sent over a limited bandwidth link. Utilizing an adaptive Z-limit as described above enables the bandwidth to be managed (via reduction of throughput requirements) while preserving the most valuable events. Once the data is transferred to the acquisition system, the method 88 includes generating (e.g., via binning or histogramming) a sinogram 107 of the accepted coincidence events (block 106). The relative sensitivity of each bin is reflected in the sinogram 107. The sinogram 107 needs to be adjusted to account for the "fractional live time" associated with the data which can be found in the list data (e.g., timing and positional data related to detection such as the coordinates for the LOR (e.g., radial distance, angles), event time-stamps, incident photon energy, etc.). The method 88 includes analyzing an increment counter for included planes (block 108) to determine factors for normalization and dead time correction. If there are $N_p$ planes in total (where $N_p=N_z*N_z-(N_z-1)$), an array of $N_p$ "live time" factors (i.e., when a particular detector was live or when events were allowed to be accepted) is all that is needed to perform normalization or dead time correction of the sinogram 107. Computationally, counting the number of intervals when a particular ring difference ($Z_{diff}$) was utilized should be sufficient to determine the correction factors. The method 88 also includes applying the live time count (i.e., "live time" factors) to perform the normalization or dead time correction on the sinogram 107 to generate a corrected and normalized sinogram 110 (block 112). The method 88 may also include performing correction for randoms on the sinogram 107 (block 114). Randoms can be estimated from the periodic singles histogram. By processing the randoms for each time interval, accounting for "missing" lines of response ("forbidden" during that particular interval because their Z difference exceeds the current threshold), and then adding all these random sinograms together, an accurate estimate can be made of the total number of randoms that were admitted during the scan; this estimate can then be used during reconstruction using methods known in the art. The method 88 further includes performing reconstruction utilizing the corrected and normalized sinogram 110 to generate a reconstructed quantitative image 116 (block 118). It should be noted that in certain embodiments listmode reconstruction may be utilized, where an actual sinogram is not generated but the relative sensitivity for each LOR needs to be known (which may be derived from the norm-deadtime correction that is created alongside the sinogram).

Rb-82 imaging of the heart is one example of a high countrate study where adaptive coincidence data processing may be useful. For Rb-82 imaging of the heart, the diagnostic quality of the exam is mostly determined by two competing factors. The first factor relates to the tracer having a very short half live (e.g., 75 seconds) and it may take several minutes for the tracer to distribute to the myocardium and clear from the blood pool. By the time the distribution image is taken, activity level may be down by 8 to 16 times compared to the injected dose. The second factor relates to obtaining an accurate analysis as the tracer needs to be injected as a bolus and a time activity curve needs to be established. In other words, there is a need for an accurate reconstruction for the first 30 seconds when the count rate is extremely high. The typical way to manage the events via randomly dropping events (e.g., throttling) is not desirable as it gives more weight than desired to random events. Utilizing the disclosed embodiments above, will give more weight to events that come out more perpendicular to the body (and that have experienced less attenuation) and improve quantitative cardiac imaging.

Figure 9:
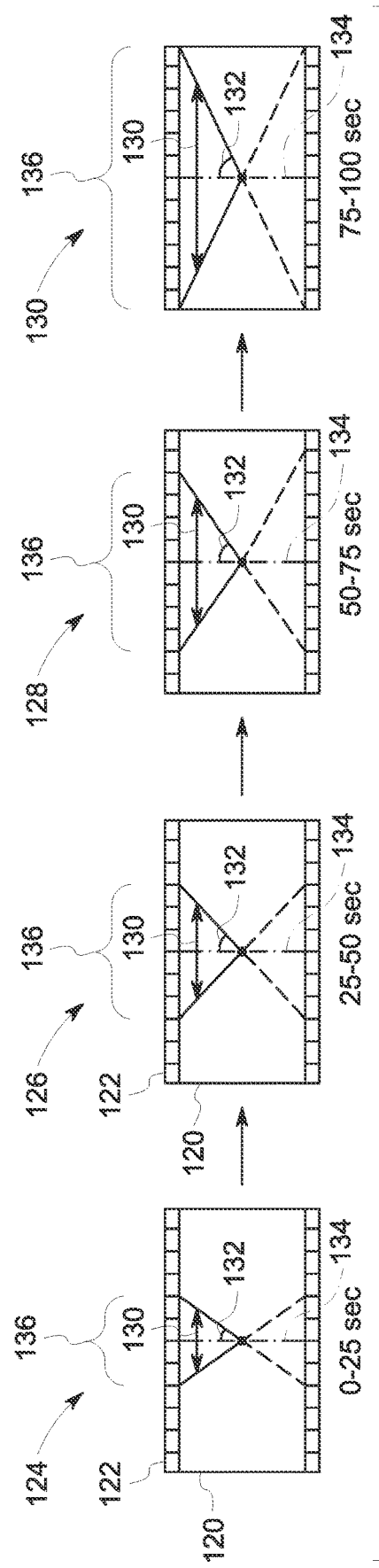
FIG. 9 is a schematic illustration for adjusting a Z span during an imaging sequence.

For example, FIG. 9 is a schematic illustration for adjusting a Z span during an imaging sequence. An axial PET scanner 120 with a number of detector rings 122 is illustrated. An imaging sequence may occur over a given time window (e.g., 100 seconds). The time window may divided into increments of 25 seconds (sec) (e.g., increments 124 (0 to 25 sec), 126 (25-50 sec), 128 (50-75 sec), and 130 (75-100 sec)) or some other increment. At the beginning of the imaging sequence (e.g., during increment 124), the activity of the tracer is at its greatest and the chance of saturation due to the number of detected events is at its greatest. During this first increment 124, a smaller $Z_{diff}$ (represented by arrow 130) may be utilized with a smaller axial angle of acceptance 132 (plus or minus) relative to a vertical plane 134 centrally located between the $Z_{diff}$ 130; thus, decreasing the overall sensitivity of the axial PET scanner 120 while preserving the more perpendicular events relative to the imaged body. During the first increment 124, detector rings 122 within a region 136 covered by the $Z_{diff}$ 130 are live (i.e., the detected events are accepted) while detector rings 122 outside the region 136 are dead (i.e., the detected events are not accepted). Over the subsequent increments 126, 128, 130, the $Z_{diff}$ 130 and the axial angle of acceptance 132 may be incrementally increased. This increase in the $Z_{diff}$ 130 and the axial angle of acceptance 132 corresponds with an increase in the number of live detector rings 122 within the region 136 (and increase in detector sensitivity) and a decrease in the number of dead detector rings 122 outside the region. In certain embodiments, it may be desirable to decrease the sensitivity of the detector over the imaging sequence. In certain embodiments, it may be desirable to alternate between increasing and decreasing the sensitivity of the detector over the imaging sequence.

Technical effects of the disclosed subject matter include providing systems and methods for dynamically adjusting the Z span of accepted events within the axial FOV of a PET scanner during a high count rate study so as to preserve the most valuable events while reducing throughput requirements. This may provide a more accurate reconstruction of a quantitative image. In addition, this may preserve sensitivity during critical phases of an imaging sequence (e.g., cardiac examination). Further, this may lower the cost and complexity of acquisition hardware. Even further, this may enable smaller file sizes to be utilized.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for adaptive coincidence data processing, comprising:
   detecting positron annihilation events with a detector array of a positron emission tomography (PET) scanner, wherein the PET scanner comprises a plurality of detector rings disposed along a longitudinal axis of the PET scanner, and each detector ring comprises a plurality of detectors; and
   within a given time period, dynamically adjusting a number of positron annihilation events accepted and transmitted to acquisition circuitry for processing utilizing a numerical difference in detector rings along the longitudinal axis between a first detector and a second detector detecting respective annihilation photons from a positron annihilation event.

2. The method of claim 1, wherein dynamically adjusting the number of positron annihilation events accepted and transmitted comprises comparing the numerical difference in detector rings for a given positron annihilation event to an acceptable numerical difference in detector rings along the longitudinal axis.

3. The method of claim 2, comprising:
   accepting and transmitting the given positron annihilation event when the numerical difference in detector rings for the given positron annihilation event falls within the acceptable numerical difference in detector rings; and
   dropping the given positron annihilation event when the numerical difference in detector rings for the given positron annihilation event falls outside the acceptable numerical difference in detector rings.

4. The method of claim 2, wherein the acceptable numerical difference in detector rings corresponds to an axial angle of acceptance for detected positron annihilation events.

5. The method of claim 2, further comprising:
comparing the number of positron annihilation events within the given time period accepted and transmitted to a threshold; and
adjusting the acceptable numerical difference in detector rings based on the comparison.

6. The method of claim 5, comprising decreasing the numerical difference in detector rings when the number of positron annihilation events within the given time period accepted and transmitted is greater than the threshold.

7. The method of claim 5, comprising increasing the numerical difference in detector rings when the number of positron annihilation events within the given time period accepted and transmitted is lesser than the threshold.

8. The method of claim 2, further comprising:
transmitting data for the accepted positron annihilation events within the given time period to the acquisition circuitry, wherein the data comprises positional and timing information related to each positron annihilation event; and
generating a sinogram from the data.

9. The method of claim 8, wherein the data comprises the numerical difference in detector rings for each accepted positron annihilation.

10. The method of claim 9, further comprising correcting the sinogram based on an amount of time each particular numerical difference in detector rings was utilized during a scan.

11. The method of claim 10, further comprising reconstructing an image from the corrected sinogram.

12. A system for adaptive coincidence data processing, comprising:
a memory encoding processor-executable routines;
a processing component configured to access the memory and to execute the processor-executable routines, wherein the routines, when executed by the processing component, cause the processing component to:
detect positron annihilation events with a detector array of a positron emission tomography (PET) scanner, wherein the PET scanner comprises a plurality of detector rings disposed along a longitudinal axis of the PET scanner, and each detector ring comprises a plurality of detectors; and
within a given time period, dynamically adjusting a number of positron annihilation events accepted and transmitted to acquisition circuitry for processing utilizing a numerical difference in detector rings along the longitudinal axis between a first detector and a second detector detecting respective annihilation photons from a positron annihilation event.

13. The system of claim 12, wherein dynamically adjusting the number of positron annihilation events accepted and transmitted comprises comparing the numerical difference in detector rings for a given positron annihilation event to an acceptable numerical difference in detector rings along the longitudinal axis.

14. The system of claim 13, wherein the routines, when executed by the processing component, cause the processing component to:
accept and transmit the given positron annihilation event when the numerical difference in detector rings for the given positron annihilation event falls within the acceptable numerical difference in detector rings; and
drop the given positron annihilation event when the numerical difference in detector rings for the given positron annihilation event falls outside the acceptable numerical difference in detector rings.

15. The system of claim 13, wherein the acceptable numerical difference in detector rings corresponds to an axial angle of acceptance for detected positron annihilation events.

16. The system of claim 13, wherein the routines, when executed by the processing component, cause the processing component to:
compare the number of positron annihilation events within the given time period accepted and transmitted to a threshold; and
adjust the acceptable numerical difference in detector rings based on the comparison.

17. The system of claim 16, wherein the routines, when executed by the processing component, cause the processing component to:
decrease the numerical difference in detector rings when the number of positron annihilation events within the given time period accepted and transmitted is greater than the threshold; and
increase the numerical difference in detector rings when the number of positron annihilation events within the given time period accepted and transmitted is lesser than the threshold.

18. The system of claim 13, wherein the routines, when executed by the processing component, cause the processing component to:
transmit data for the accepted positron annihilation events within the given time period to the acquisition circuitry, wherein the data comprises positional and timing information related to each positron annihilation event and the numerical difference in detector rings for each accepted positron annihilation; and
generate a sinogram from the data.

19. The system of claim 18, wherein the routines, when executed by the processing component, cause the processing component to correct the sinogram based on an amount of time each particular numerical difference in detector rings was utilized during a scan.

20. A non-transitory computer-readable medium, the computer-readable medium comprising processor-executable code that when executed by a processor, causes the processor to:
detect positron annihilation events with a detector array of a positron emission tomography (PET) scanner, wherein the PET scanner comprises a plurality of detector rings disposed along a longitudinal axis of the PET scanner, and each detector ring comprises a plurality of detectors; and
within a given time period, dynamically adjust a number of positron annihilation events accepted and transmitted to acquisition circuitry for processing utilizing a numerical difference in detector rings along the longitudinal axis between a first detector and a second detector detecting respective annihilation photons from a positron annihilation event by comparing the numerical difference in detector rings for a given positron annihilation event to an acceptable numerical difference in detector rings along the longitudinal axis, wherein the acceptable numerical difference in detector rings corresponds to an axial angle of acceptance for detected positron annihilation events.

* * * * *